US005629463A

United States Patent [19]
Ardito et al.

[11] Patent Number: 5,629,463
[45] Date of Patent: May 13, 1997

[54] NAPHTHALENE ALKYLATION WITH RE AND MIXED H/NH3 FORM CATALYST

[75] Inventors: Susan C. Ardito, Spring Lake Hts; Henry Ashjian, E. Brunswick; Thomas F. Degnan, Moorestown, all of N.J.; Terry E. Helton, Glen Mills, Pa.; Quang N. Le, Singapore, Singapore; Augusto R. Quinones, Wilmington, Del.

[73] Assignee: Mobil Oil Corporation, Fairfax, Va.

[21] Appl. No.: 519,381

[22] Filed: Aug. 25, 1995

Related U.S. Application Data

[63] Continuation-in-part of Ser. No. 172,300, Dec. 23, 1993, abandoned, which is a continuation-in-part of Ser. No. 173,006, Dec. 27, 1993, Pat. No. 5,457,254.

[51] Int. Cl.$^6$ .............................. C07C 2/64; C07C 2/66; C07C 15/107
[52] U.S. Cl. ..................... 585/455; 585/446; 585/467
[58] Field of Search .................... 585/446, 455, 585/467

[56] References Cited

U.S. PATENT DOCUMENTS

| | | | |
|---|---|---|---|
| 4,570,027 | 2/1986 | Boucher et al. | 585/455 |
| 5,034,563 | 7/1991 | Ashjian et al. | 585/455 |
| 5,457,254 | 10/1995 | Ardito et al. | 585/455 |

Primary Examiner—Glenn A. Caldarola
Assistant Examiner—Elizabeth D. Wood
Attorney, Agent, or Firm—M. D. Keen; B. E. Loo

[57] ABSTRACT

Long chain alkyl substituted naphthalenes are produced by alkylating naphthalene with an olefin or other alkylating agent with at least 6, and usually 12 to 20 carbon atoms, in the presence of an alkylation catalyst comprising a zeolite having rare earth cations, and both ammonium and protonic species, associated with the exchangeable sites of the zeolite. The zeolite is usually a large pore size zeolite such as USY. The presence of rare earths and both ammonium and protonic species increases selectivity for production of long chain mono-alkyl substituted naphthalenes in preference to more highly substituted products.

19 Claims, No Drawings

NAPHTHALENE ALKYLATION WITH RE AND MIXED H/NH3 FORM CATALYST

CROSS-REFERENCE TO RELATED APPLICATIONS

This application is a continuation-in-part of both U.S. patent application Ser. No. 08/172,300 filed Dec. 23, 1993, now abandoned, and U.S. patent application Ser. No. 08/173,006 filed Dec. 27, 1993, now U.S. Pat. No. 5,457,254.

Both applications are incorporated by reference.

FIELD OF THE INVENTION

This invention relates to a process for preparing long chain alkyl substituted naphthalenes.

BACKGROUND OF THE INVENTION

Alkylaromatic fluids have been proposed as functional fluids where good thermal and oxidative stability are required.

U.S. Pat. No. 4,714,794 (Yoshida) describes monoalkylated naphthalenes as having excellent thermal and oxidative stability, low vapor pressure and flash point, good fluidity, high heat transfer capacity and other properties which render them suitable for use as thermal medium oils.

The use of a mixture of monoalkylated and polyalkylated naphthalenes as a base for synthetic functional fluids is described in U.S. Pat. No. 4,604,491 (Dressler). Pellegrini U.S. Pat. Nos. 4,211,665 and 4,238,343 teaches use of alkylaromatics as transformer oils.

Alkylated naphthalenes are usually produced by alkylating naphthalene or a substituted naphthalene in the presence of an acidic alkylation catalyst such as a Friedel-Crafts catalyst. Acidic clay was used in Yoshida U.S. Pat. No. 4,714,794 while aluminum trichloride was used in Pellegrini U.S. Pat. Nos. 4,211,665 and 4,238,343.

A collapsed silica-alumina zeolite catalyst for alkylation of naphthalene was disclosed in Boucher U.S. Pat. No. 4,570,027. Use of intermediate pore zeolites such as ZSM-5 and large pore zeolites such as zeolite L and ZSM-4 for alkylation of benzene is disclosed in Young U.S. Pat. No. 4,301,316.

For functional fluids based on alkyl naphthalenes, it the preferred alkyl naphthalenes are mono-substituted. They provide the best combination of properties in the finished product and have fewer benzylic hydrogens than corresponding di-substituted or polysubstituted versions and have better oxidative stability. In addition, mono-substituted naphthalenes have a kinematic viscosity in the desirable range of about 5–8 cSt (at 100° C.) when working with alkyl substituents of about 14 to 18 carbon atoms chain length. Although mono-alkylated naphthalenes may be obtained in admixture with more highly alkylated naphthalenes using conventional Friedel-Crafts catalysts or by the use of zeolites such as USY, the selectivity to the desired mono-alkylated naphthalenes is not as high as desired.

Several recent advances have been made in this area which improve the yields of the desired mono-alkylated naphthenes.

U.S. Pat. No. 5,034,563, Ashjian et al, which is incorporated by reference, teaches use of a zeolite containing a bulky cation. The use of, e.g., USY with cations having a radius of at least about 2.5 Angstroms increases selectivity for desired products. Taught as suitable were zeolites containing hydrated cations of metals of Group IA, divalent cations, especially of Group IIA, and cations of the Rare Earths. H, NH4, Na were added to USY zeolite by forming a slurry of zeolite and liquid, 1 hour of stirring, decantation, and a repeat of the exchange procedure.

U.S. Pat. No. 5,177,284, Le et al, which is incorporated by reference, discussed the desirable properties of alkylated naphthalene fluids with higher alpha:beta ratios, including improved thermal and oxidative stability. Le et al found that several parameters influenced the alpha:beta ratio of the alkylated naphthalene products, including steaming the zeolite, lowering the alkylation temperature; or use of acid-treated clay. Steamed USY catalyst gave excellent results in the examples. The patentees mentioned use of zeolites with reduced activity due to base exchange, alkaline earth ion exchange and use of boron-zeolite beta.

U.S. Pat. No. 5,191,135 Dwyer et al, which is incorporated by reference, disclosed co-feeding water when using a large pore zeolite catalyst, such as zeolite Y. Adding from 1–3 wt % water to the feed improved the alkylation reaction, a result attributed to suppression of zeolite acid site activity.

U.S. Pat. No. 5,191,134, Le, which is incorporated by reference, disclosed a similar alkylation process using MCM-41.

We did additional work to see if we could further improve this alkylation process. We wanted to increase the efficiency of the reaction both in terms of conversion and yields.

We discovered that catalyst containing controlled amounts of NH4 and H and rare earths gave unexpectedly superior results. Phrased another way, catalyst with a limited amount of rare earths, exchanged with ammonia and then only about half calcined, gave better results than a like catalyst which was left wholly in the ammonium form, or calcined to be in the protonic form.

SUMMARY OF THE INVENTION

Accordingly, the present invention provides a process for preparing long chain alkyl substituted naphthalenes comprising alkylating a naphthalene with an alkylating agent possessing an alkylating aliphatic group having at least six carbon atoms under alkylation reaction conditions in the presence of an alkylation catalyst comprising a porous crystalline zeolite containing exchangeable sites; and both ammonium and protonic species and rare earths associated with said exchangeable sites, and wherein the ratio of ammonium:protonic species is within the range of 95:5 to 5:95, molar basis, and wherein at least some but less than 50% of the total number of exchangeable sites is associated with Rare Earths to form an alkylated naphthalene possessing at least one alkyl group derived from the alkylating agent.

In another embodiment, the present invention provides a process for preparing long chain alkyl substituted naphthalenes comprising alkylating naphthalene with an olefin containing at least 8 carbon atoms under alkylation reaction conditions in the presence of an alkylation catalyst comprising an ultrastable Y zeolite with exchangeable sites containing both ammonium and protonic species at a molar ratio of ammonium:protonic species from 65:35 to 35:65, and wherein the zeolite is 12.5 to 17.5% Rare Earth exchanged, to form an alkylated naphthalene.

DETAILED DESCRIPTION

The starting materials for the production of the alkylated naphthalenes are naphthalene itself as well the substituted naphthalenes which may contain one or more short chain alkyl groups containing up to about eight carbon atoms, such as methyl, ethyl or propyl. Suitable alkyl-substituted naphthalenes include alpha-methylnaphthalene, dimethylnaphthalene and ethylnaphthalene. Naphthalene itself is preferred since the resulting mono-alkylated products have better thermal and oxidative stability than the more highly alkylated materials for the reasons set out above.

The alkylating agents used include any aliphatic or aromatic organic compound having one or more available alkylating aliphatic groups capable of alkylating the naphthalene. The alkylatable group itself should have at least about 6 carbon atoms, preferably at least about 8, and still more preferably at least about 12 carbon atoms. For use in functional fluids and additives, the alkyl groups on the alkyl-naphthalene preferably have from 12 to 30 carbon atoms, more preferably 14 to 18 carbon atoms. Preferred alkylating agents are the olefins with the requisite number of carbon atoms, for example, the hexenes, heptenes, octenes, nonenes, decenes, undecenes, dodecenes. Mixtures of olefins, e.g. mixtures of $C_{12}$–$C_{20}$ or $C_{14}$–$C_{18}$ olefins, are useful. Branched alkylating agents, especially oligomerized olefins such as the trimers, tetramers, pentamers, etc., of light olefins such as ethylene, propylene, the butylenes, etc., are also useful. Other useful alkylating agents which may be used, although less easily, include alcohols and the like.

The alkylation reaction between the naphthalene and the alkylating agent is carried out in the presence of a zeolite catalyst which contains a cation of certain specified radius. The molecular size of the alkylation products will require a relatively large pore size in the zeolite in order for the products to leave the zeolite, indicating the need for a relatively large pore size in the zeolite, which will also tend to reduce diffusion limitations with the long chain alkylating agents. The large pore size zeolites are the most useful zeolite catalysts for this purpose although intermediate pore size zeolites may also be used, as discussed below.

The large pore size zeolites are zeolites such as faujasite, the synthetic faujasites (zeolites X and Y), zeolite L, ZSM-4, ZSM-18, ZSM-20, mordenite and offretite.

They are characterized by the presence of a 12-membered oxygen ring system in the molecular structure and by the existence of pores with a minimum dimension of at least 7.4 Å, as described by Frilette et al. in *J. Catalysis* 67,218–222 (1981). See also Chen et al. *Shape-Selective Catalysis in Industrial Applications,* (Chemical industries; Vol. 36) Marcel Dekker Inc., New York 1989, ISBN 0-8247-7856-1 and Hoelderich et al. *Angew. Chem. Int. Ed. Engl.* 27 226–246 (1988), especially pp. 226–229. The large pore size zeolites may also be characterized by a "Constraint Index" of not more than 2, in most cases not more than 1. Zeolite beta has a structure characterized by twelve-membered pore openings, although under certain circumstances it has a Constraint Index approaching 2. The method for determining Constraint Index is described in U.S. Pat. No. 4,861,932.

Zeolites with a ten membered oxygen ring, generally regarded as the intermediate pore size zeolites may also be effective catalysts for this alkylation reaction if their structure is not too highly constrained. Thus, ZSM-12 (Constraint Index 2) may be effective for this reaction. The zeolite identified as MCM-22 is a useful catalyst for this reaction. MCM-22 is described in U.S. Pat. No. 4,962,239. Zeolites having a CI up to about 3 will generally be useful catalysts, although the activity depend on the alkylating agent, especially its chain length, a factor which imposes diffusion limitations upon the choice of zeolite.

A preferred zeolite is ultrastable Y, usually referred to as USY. When this material contains (H+NH3+RE) it catalyses the alkylation in good yields with excellent selectivity. Zeolite USY is a material of commerce, available in large quantities as a catalyst for the cracking of petroleum. It is produced by repeated ammonium exchange and controlled steaming of zeolite Y. Production of USY is described in U.S. Pat. Nos. 3,402,966 (McDaniel), 3,923,192 (Maher) and 3,449,070 (McDaniel).

We prefer to use a small crystal Y zeolite, in the 0.2 to 0.4 micron range, although the 0.6 to 1.3 micron material which is more typical of Y zeolite crystals may also be used.

AMMONIUM EXCHANGE/CALCINATION

It is essential to put the zeolite in a form in which the cation exchange sites contain both ammonium and protonic species. Expressed as % of total (ammonium+protonic species), the ratio of ammonium:protonic species is within the range of 95:5 to 5:95, molar basis. Preferably, the ratio of ammonium:protonic species is within the range of 65:35 to 35:65, molar basis. More preferably, the ammonium and protonic forms each occupy at least 40% of the total (ammonium+protonic species). Most preferably, the ammonium form is 55 to 50%, with the protonic form being the remainder of the total (ammonium+protonic species), i.e. at a ammonium:protonic species ratio of 55:45 to 50:50.

This ratio, ammonium:protonic, may also be expressed in terms of a standardized calcination procedure after ammonium exchange. Thus the zeolite may be placed in the ammonium form using conventional techniques. Typically this involves contacting the zeolite, or catalyst, with 5 vol/vol of N N NH4NO3 and stirring for an hour, water washing, another exchange step, and a final wash. The catalyst then may be calcined for 5 hours in flowing air. When this procedure is used, calcining at 400°–425° C. gives optimum results.

The above ratios, of ammonium to protonic forms hold even in the presence of Rare Earths, which reduce the total amount of ammonium and protonic ions present, but do not alter the critical ratio of ammonium:protonic species.

RARE EARTH EXCHANGE

The selected zeolite catalyst must contain a controlled amount of one or more Rare Earths. Suitable are Y, La and any of the Lanthanum Series of Rare Earths, Ce, Pr, Nd, Pm, Sm, Eu, Gd, Tb, Dy, Ho, Er, Tm Yb, and Lu. Especially preferred are Ce, Y and La. Usually mixtures of rare earths will be preferred, as these are readily available commercially and less expensive than purified rare earth elements. The mixed rare earths typically used to produce zeolite Y based cracking catalysts serve well.

If the zeolite does not contain the desired amount of rare earths they may be introduced by ion-exchange in the conventional manner using a solution of the exchanging cation.

It is essential to have some, but less than 50%, of the exchangeable sites associated with Rare Earths. Preferably at least 5% but less than 45% of the exchangeable sites contain Rare Earths, and most preferably at least 20% but less than about 40%. Optimum results are seen with 25 to 36% Rare Earth exchange. Total ion exchange capacity may be determined by temperature programmed ammonia desorption as described by G. T. Kerr and A. W. Chester in Thermochimica Acta, 3, 113–124 (1971), which is incorporated by reference.

For a typical catalyst, comprising 40 wt % USY zeolite in a conventional binder or matrix as discussed below, the optimum RE content is about 1 wt %, equivalent to a rare earth content of about 25% of the total number of exchangeable sites.

Binders may be used to improve crush strength and physical properties. Suitable materials include naturally occurring clays, e.g., bentonite and kaolin as well as silica, alumina etc.

The relative proportions of zeolite, present in finely divided crystalline form, and oxide matrix may vary widely, with the crystalline zeolite content ranging from about 1 to about 90 percent by weight and more usually, particularly when the composite is prepared in the form of beads, in the range of about 2 to about 80 weight percent of the composite.

The stability of the alkylation catalyst of the invention may be increased by steaming. U.S. Pat. Nos. 4,663,492; 4,594,146; 4,522,929; and 4,429,176, describe steam stabilization of zeolite catalysts. Care should be taken to ensure that steaming conditions are not so severe as to convert too much of the ammonium species to protonic species.

ALKYLATION REACTION CONDITIONS

The alkylation process of this invention is conducted such that the alkylatable aromatic compound and the alkylating agent, are contact the catalyst in a suitable reaction zone, e.g., a reactor containing a fixed bed of catalyst under alkylation conditions. Such conditions typically include a temperature of from 100° C. to 400° C., a pressure from 0.2 to 250 atmospheres, a feed weight hourly space velocity (WHSV) of 0.1 hr$^{-1}$ to 10 hr$^{-1}$ and an alkylatable aromatic compound to alkylating agent mole ratio of 0.1:1 to 50:1, preferably from 4:1 to 1:4, and most preferably from 2:1 to 1:2. The WHSV is based upon the total weight of active catalyst (and binder if present).

Preferred reaction conditions include a temperature of 100° C. to 350° C., a pressure of 1 to 25 atmospheres, a WHSV of 0.5 hr$_{-1}$ to 5 hr$_{-1}$. More preferably, alkylation reaction conditions include a temperature of 100° C. to 300° C., a pressure of 1 to 5 atmospheres, and an alkylatable aromatic:alkylating agent mole ratio of 0.5:1 to about 5:1. When using naphthalene as the aromatic, the pressure should be at least 50 psig to prevent the naphthalene from subliming. Pressure may be maintained by inert gas blanketing, preferably with nitrogen. The reactants can be in vapor or liquid phase and can be neat, i.e., free from dilution with other material, or they can be brought into contact with the zeolite catalyst composition with the aid of carrier gases or diluents such as, for example, hydrogen or nitrogen.

Alkylation can be carried out as a batch-type reaction typically employing a pressurized, stirred reactor with an inert gas blanketing system or in a semi-continuous or continuous reactor using a fixed, moving or fluidized bed catalyst system.

The presence of some water may improve selectivity, e.g., operation with water addition to the feed or hydration of the catalyst. For a fluid bed reactor operation with about 0.75 wt % water in the reaction mixture is preferred.

The products comprising alkylated aromatics are characterized by exceptional oxidative and thermal stability. They may be separated from the reaction mixture by stripping off unreacted alkylating agent and naphthalene compound in the conventional manner. Stability of alkylated product may be improved by filtration over activated charcoal and by alkali treatment to remove impurities, especially acidic by-products formed by oxidation during the reaction.

EXAMPLE 1

A commercially available catalyst containing 40 wt. % USY (Unit Cell Size=24.45 A) in a clay and silica sol matrix was ammonium exchanged at room temperature by slurrying the catalyst with 5 vol/vol of 1N NH$_4$NO$_3$ for one hour. The catalyst was washed with water and then reexchanged and washed using the same procedure. This catalyst was then calcined for 5 hours in flowing air at a series of temperatures ranging from 350° C. to 538° C. to produce catalysts containing varying amounts of ammonia. The relative amounts of cation exchange sites in the ammonium and protonic form are shown below:

| Catalyst ID | Calcination Temperature, °C. | NH$_4^+$ Conc. (meq/g) | H$^+$ Conc. (meq/g) |
| --- | --- | --- | --- |
| A | None | 1.09 | 0 |
| B | 350 | 0.85 | 0.24 |
| C | 375 | 0.64 | 0.45 |
| D | 400 | 0.59 | 0.50 |
| E | 425 | 0.54 | 0.55 |
| F | 450 | 0.34 | 0.75 |
| G | 538 | 0 | 1.09 |

The total ion exchange capacity of the catalyst as determined by temperature programmed ammonia desorption (Chester and Kerr method) is 1.09 meq/g.

EXAMPLE 2

In a series of six experiments, five parts of each of the catalysts of Example 1 were combined with ninety-five parts of naphthalene and 1-hexadecene in a 1:1.2 molar ratio in a stirred vessel. The contents of the vessel were then heated to 200° C. and held at this temperature for four hours. The contents of the vessel were analyzed using gas chromatography to determine the amounts of unreacted naphthalene, olefin, monoalkylate and dialkylate. The results are summarized below:

| Catalyst ID | Naphthalene (wt. %) | Hexadecene (wt. %) | Monoalkylate (wt. %) | Dialkylate (wt. %) |
| --- | --- | --- | --- | --- |
| A | 32.3 | 67.7 | 0 | 0 |
| B | 20.3 | 42.6 | 37.0 | 0 |
| C | 15.5 | 35.7 | 48.3 | 0.5 |
| D | 6.3 | 19.2 | 72.9 | 1.6 |
| E | 13.5 | 30.1 | 55.4 | 1.0 |
| F | 12.2 | 29.6 | 56.6 | 1.6 |
| G | 12.9 | 27.7 | 59.1 | 0.3 |

The above results show that Catalyst D, the catalyst with the ammonium cation concentration of 0.59 meq/g, is the most effective catalyst for this reaction. Only 54% of the exchangeable sites of this catalyst are in the ammonium form, the remainder are in the hydrogen form. This example demonstrates that only a fraction of the exchangeable sites need to contain a cation for the catalyst to be effective.

EXAMPLE 3

A commercially available USY with the properties shown below was combined with kaolin clay and a colloidal silica (Nalco) and spray dried at a temperature of 177° C. (350° F.) to produce a fluid catalyst containing 40 wt. % USY.

| | |
|---|---|
| UC Lattice Parameter, A | 24.29 |
| Surface Area, m²/g | 650 |
| Sodium, ppm | 445 |
| $SiO_2$, wt. % | 85.8 |
| $Al_2O_3$, wt. % | 10.8 |
| $SiO_2/Al_2O_3$ (molar) | 13.8 |
| Ash at 1000° C. | 98.7 |
| Real Density, g/cc | 2.384 |
| Sorption Capacities** | |
| n-$C_6$ (p = 40 torr) | 21.1 |
| Cy-$C_6$ (p = 40 torr) | 19.8 |
| $H_2O$ (p = 12 torr) | 10.6 |

*Surface area measured at $P/P_o$ = 0.03
**Sorption Capacities are shown as wt ratios × 100 (= wt of sorbate × 100/wt of sorbate free zeolite)

This catalyst was ion exchanged with ammonium nitrate using the procedure described in Example 1 and then calcined at 400° C. in flowing air for five hours to produce Catalyst H. Another catalyst, Catalyst I, was prepared from the same base ammonium exchanged material by calcining at 538° C. in flowing air for five hours.

The ammonia content and water content of these catalysts were analyzed by TPAD and by determination of loss on ignition at 700° C. The results are summarized below:

| Catalyst ID (wt. %) | Calcination Temperature, °C. | $NH_4^+$ Conc. (meq/g) | $H^+$ Conc. (meq/g) | $H_2O$ Conc. |
|---|---|---|---|---|
| H 2.0 | 400 | 0.04 | 0.06 | |
| I 0.1 | 538 | 0 | 0.10 | |

EXAMPLE 4

Five parts of each of the catalysts of Example 3 were combined with ninety-five parts of naphthalene and 1-hexadecene in a 1:1.2 molar ratio in a stirred vessel. The contents of the vessel were then heated to 200° C. and held at this temperature for four hours. The contents of the vessel were analyzed using gas chromatography to determine the amounts of unreacted naphthalene, olefin, monoalkylate and dialkylate. The results are summarized below:

| Catalyst | Dialkylate (wt. %) | Naphthalene ID (wt. %) | Hexadecene (wt. %) | Monoalkylate | |
|---|---|---|---|---|---|
| | | | | (wt. %) | (wt. %) |
| H | 3.1 | 8.3 | 79.7 | 8.9 | |
| I | 4.9 | 5.9 | 63.0 | 26.2 | |

The results show that only a small amount of ammonia (0.04 meq/g, 40% of the exchangeable sites) is necessary to modify the selectivity of the reaction and produce more of the highly desirable monoalkylate.

EXAMPLE 5

Five parts of Catalyst J, a commercially available rare earth containing USY (REUSY) catalyst having the properties shown below were combined with ninety-five parts of naphthalene and 1-hexadecene in a 1:1.2 molar ratio in a stirred vessel.

| Properties of the Catalyst Used in This Example | |
|---|---|
| $RE_2O_3$ content, wt. % | 1.0 |
| % RE Exchange | 25 |
| Unit Cell Lattice Parameter, A | 24.57 |
| Ammonia Content, meq/g | 0.56 |
| Ash, wt. % (at 700° C.) | 89.5 |

The contents of the vessel were then heated to 200° C. and held at this temperature for four hours. The contents of the vessel were analyzed using gas chromatography to determine the amounts of unreacted naphthalene, olefin, monoalkylate and dialkylate. The results are summarized below:

| Catalyst | Dialkylate (wt. %) | Naphthalene ID (wt. %) | Hexadecene (wt. %) | Monoalkylate | |
|---|---|---|---|---|---|
| | | | | (wt. %) | (wt. %) |
| J | 2.5 | 13.6 | 82.1 | 1.8 | |

EXAMPLE 6

Five parts of Catalyst K, a commercially available rare earth containing USY (REUSY) catalyst having the properties shown below were combined with ninety-five parts of naphthalene and 1-hexadecene in a 1:1.2 molar ratio in a stirred vessel.

| Properties of the Catalyst Used in This Example | |
|---|---|
| $RE_2O_3$ content, wt. % | 3.0 |
| % RE Exchange | 36 |
| Unit Cell Lattice Parameter, A | 24.57 |
| Ammonia Content, meq/g | 0.74 |
| Ash, wt. % (at 700° C.) | 87 |

The vessel was heated to 200° C. for four hours. The contents were analyzed using gas chromatography to determine unreacted naphthalene, olefin, monoalkylate and dialkylate. The results are summarized below:

| Catalyst | Dialkylate (wt. %) | Naphthalene ID (wt. %) | Hexadecene (wt. %) | Monoalkylate | |
|---|---|---|---|---|---|
| | | | | (wt. %) | (wt. %) |
| K | 24.3 | 50.2 | 25.0 | 0.5 | |

Comparison of the results of Examples 5 and 6 show that the rare earth content of the catalysts can affect yields and that the lower rare earth concentration (i.e., 1 wt. %) is preferred. The rare earth content of the preferred catalyst (Example 5) catalyst would correspond to about 25% of the total number of exchangeable sites.

EXAMPLE 7

Zeolite Y Crystals

Six different samples of Zeolite Y crystals were used in this study to ascertain the effects of sodium level and framework $SiO_2/Al_2O_3$ ratio (or alternatively, Unit Cell Size, or UCS). These samples had a somewhat smaller crystal size than other Y zeolite, from 0.2 to 0.4 microns v. 0.6 to 1.3 microns for typical Y zeolite. The samples were:

HSZ-320NAA—Standard NaY zeolite (UCS=~24.64 A)
HSZ-320HOA—Partially NH$_4^+$ exchanged and calcined NaHY
HSZ-330NHA—Low sodium, ammonium form of USY (UCS=~24.50 A)
HSZ-330HSA—Low sodium, H-form of USY (UCS=~24.50 A)
HSZ-330HUA—Low sodium, lower UCS H-form USY (UCS=~24.40 A)
HSZ-360HUA—High silica USY, very low Na (UCS=~24.30 A)

Properties of as-received crystals are given in Table 1.

Matrix

The zeolites were incorporated into a silica-clay matrix at a 40 wt. % zeolite level. To produce this matrix, one part of colloidal silica (Nalco 1034A) was mixed with one part of a Thiele RC-32 clay, charged as a slurry. The zeolite was added to the clay-silica mixture and the formulation was spray dried at 350° F., pH=3 to 4.5 and then either calcined at 1000° F. or ammonium exchanged twice with 1N NH$_4$NO$_3$ solution, 5 volume of solution/volume catalyst, and then calcined as described below.

Final Calcination

The ammonium exchanged samples were calcined at either 572° F. (300° C.) or 752° F. (400° C.) to leave different levels of ammonia on the catalysts. The calcination consisted of heating the samples in flowing air (5 vol air/vol catalyst/min) from room temperature to the target temperature at 5° F./min. The catalysts were then held at the final temperature in flowing air for 5 hours. The fully calcined samples (1000° F.) were produced in a similar manner but were not ammonium exchanged prior to final calcination.

Analysis of Reaction Products

All alkylation runs were carried out in stirred flasks at 392° F. (200° C.). The runs consisted of charging the naphthalene and 1-hexadecene (in a 1:1.2 molar ratio). The catalyst was then charged and the mixture was heated to the reaction temperature. Samples were taken at 2, 4, 6, and 8 hours and analyzed by GC. The amount of dimer was difficult to ascertain since it co-eluted with the monoalkylated naphthalene. In an attempt to deconvolute the amount of dimer and alkylated naphthalene, we calculated a predicted naphthalene and C$_6$=Conversion based upon the analysis of the mono- and dialkylated naphthalenes. When the naphthalene conversion was higher than that measured from the naphthalene peak area, the excess was assumed to be dimer. This was the convention used to calculate the conversions shown in the tables below.

TPAD Analysis

Temperature programmed ammonia desorption was carried out using the method described by Kerr and Chester. Typically, the sample was heated in the DuPont Model 951 TGA from room temperature to 700° C. at 10° C./minute under a 150 ml/minute flow of high purity helium. The stream of helium containing the desorbed ammonia was passed through a buffered solution where the excess base was titrated with sulfamic acid solution of known concentration (usually ~0.017 g N/l). The exchange capacity is reported as milliequivalents of ammonia per gram of catalyst (meq/g) based on the weight of the catalyst determined at 700° C.

|  | 752° F. Calcined Samples | | | | | |
|---|---|---|---|---|---|---|
| ZEOLITE Y SAMPLE | 320NAA | 320HOA | 330HUA | 330HSA | 330NHA | 360HUA |
| Ash, wt. % | 93.4 | 93.3 | 94.2 | 93.7 | 93.8 | 94.6 |
| Na, wt. % (as-rec'd) | 0.89 | 1.00 | 0.069 | 0.047 | 0.066 | 0.055 |
| Na, wt. % (dry) | 0.95 | 1.07 | 0.073 | 0.050 | 0.070 | 0.058 |
| N, wt. % (as-rec'd) | 0.46 | 0.55 | 0.21 | 0.50 | 0.61 | 0.11 |
| N, wt. % (dry) | 0.49 | 0.59 | 0.23 | 0.53 | 0.65 | 0.12 |
| meq NH$_3$/g Cat[1] | 0.35 | 0.42 | 0.16 | 0.38 | 0.46 | 0.086 |
| meq Na/g Cat | 0.41 | 0.47 | 0.03 | 0.02 | 0.03 | 0.02 |
| meq NH$_3$/g USY[2] | 0.875 | 1.05 | 0.40 | 0.95 | 1.15 | 0.215 |
| meq Na/g USY[2] | 1.025 | 1.175 | 0.075 | 0.050 | 0.075 | 0.050 |
| meq (Na + NH$_3$)/g USY[2] | 1.90 | 2.23 | 0.475 | 1.00 | 1.23 | 0.265 |
| As-Received Properties | | | | | | |
| TPAD, meq NH$_4^+$/g CAT | 0.25 | 0.34 | 0.10 | 0.30 | 0.28 | 0.04 |
| TPAD, meq NH$_4^+$/g USY[2] | 0.625 | 0.85 | 0.25 | 0.75 | 0.70 | 0.10 |
| Catalyst Exch. Capac., (meq NH$_4^+$/g Cat) |  | 0.89 | 0.18 | 0.38 | 0.52 | 0.10 |
| USY Exch. Capac., (meq NH$_4^+$/g USY) |  | 2.23 | 0.45 | 0.95 | 1.30 | 0.25 |
| As-Rec'd NH$_4^+$ as % of Total Exch. Capac. |  | 38 | 56 | 79 | 54 | 40 |
| Naphthalene Conv.[3], % | 98 | 96 | 83 | 89 | 87 | 95 |
| Olefin (C$_{16}$=) Conv.$_{-3}$, % | 84 | 82 | 72 | 77 | 78 | 87 |
| Dialkylnaph. Select.[3], % | 2 | 3 | 5 | 4 | 7 | 10 |
| Computed occupancies[4], vol. % NH$_4^+$ (based on TPAD) | 34 | 46 | 14 | 41 | 38 | 5 |

Notes:
[1] Ammonia content based on elemental analysis of nitrogen on the catalyst
[2] Assumes that catalyst contain 40 wt. % USY
[3] 8 hours on stream, 200° C., Naphthalene:C$_{16}$= = 1:1.2 (molar), 5 wt. % catalyst
[4] Na is assumed to be in sodalite cages following calcination and ammonium exchange.

| | 1000° F. Calcined Samples | | | | | |
|---|---|---|---|---|---|---|
| Zeolite Y Sample | 320NAA | 320HOA | 330HUA | 330HSA | 330NHA | 360HUA |
| Ash, wt. % | 96.6 | 96.8 | 95.6 | 95.4 | 97.6 | 98.1 |
| Na, wt. % (as-rec'd) | 3.55 | 4.30 | 0.145 | 0.147 | 0.157 | 0.132 |
| Na, wt. % (dry) | 3.68 | 4.44 | 0.152 | 0.154 | 0.160 | 0.134 |
| meq Na/g Cat | 1.60 | 1.93 | 0.066 | 0.066 | 0.069 | 0.058 |
| meq Na/g USY | 4.00 | 4.83 | 0.165 | 0.165 | 0.173 | 0.145 |
| Wt. % USY (XRD) | 42 | 33 | 42 | 42 | 41 | 40 |
| meq Na/g USY (XRD) | 3.80 | 5.84 | 0.157 | 0.160 | 0.171 | 0.146 |
| Unit Cell Parameter, A | 24.60 | 24.60 | 24.34 | 24.44 | 24.44 | 24.26 |
| Al/(Si + Al) | 0.214 | 0.214 | 0.0606 | 0.1196 | 0.1196 | 0.0134 |
| Theo. Exch. Capac.[1] (meq Na/g USY) | 4.58 | 4.58 | 1.06 | 2.08 | 2.08 | 0.233 |
| As-Rec'd Na as % of Total Exch. Capac. | 83 | 105 | 15.6 | 7.7 | 8.2 | 62.7 |
| Naphthalene Conv.[2], % | 34 | 40 | 81 | 83 | 85 | 92 |
| Olefin ($C_{16}^=$) Conv.[2], % | 28 | 34 | 82 | 85 | 86 | 92 |
| Dialkylnaph. Select.[2], % | 0 | 0 | 21 | 23 | 22 | 21 |

Notes:
[1] Computed; Al/(Al + Si) = 0.59 $a_o$(A) − 14.3
[2] 8 hours stream, 210° C., Naphthalene:$C_{16}^=$ = 1:1.2 (molar), 5 wt. % catalyst.

These data show optimum performance when the zeolite contains ammonium and protonic cations on the exchangeable sites and some rare earths. Some water is beneficial too, but the amount of water in most commercial grade naphthalene supplies (typically 0.75 wt %) is enough.

We claim:

1. A process for preparing long chain alkyl substituted naphthalenes which comprises:

alkylating a naphthalene with an alkylating agent possessing an alkylating aliphatic group having at least six carbon atoms under alkylation reaction conditions in the presence of an alkylation catalyst comprising a porous crystalline zeolite;

said zeolite containing exchangeable sites, and ammonium and protonic species and rare earths associated with said exchangeable sites;

wherein the ratio of ammonium:protonic species is within the range of 95:5 to 5:95, molar basis, and at least some but less than 50% of the total number of exchangeable sites contain Rare Earths; and forming an alkylated naphthalene possessing at least one alkyl group derived from the alkylating agent.

2. The process of claim 1 wherein the zeolite is a large pore size zeolite having pores with a minimum dimension of at least 7.4 Å.

3. A process according to claim 1 wherein the zeolite is 5 to 45% Rare Earth exchanged.

4. The process of claim 1 wherein the zeolite comprises zeolite X or zeolite Y.

5. The process of claim 4 wherein the zeolite is USY.

6. The process of claim 1 wherein the ratio of ammonium:protonic species is 90:10 to 10:90.

7. The process of claim 1 wherein the ratio of ammonium:protonic species is 65:35 to 35:65.

8. The process of claim 1 wherein the ratio of ammonium:protonic species is about 55:45 to 50:50.

9. The process of claim 1 wherein the alkylating aliphatic group contains at least about 8 carbon atoms.

10. The process of claim 9 wherein the alkylating aliphatic group contains at least about 12 carbon atoms.

11. The process of claim 10 wherein the alkylating aliphatic group contains from 14 to 20 carbon atoms.

12. The process of claim 1 wherein the alkylating agent comprises an olefin.

13. The process of claim 1 wherein the alkylation reaction conditions include a temperature of 100° C. to 400° C. pressure of 0.2 to 25 atmospheres, a WHSV of 0.1 $hr^{-1}$ to 10 $hr^{-1}$ and an alkylatable aromatic:alkylating agent mole ratio of 0.1:1 to 50:1.

14. The process of claim 13 wherein alkylation reaction conditions include a temperature of 100° C. to 300° C., a pressure of 1 to 5 atmospheres, a WHSV of 0.5 $hr^{-1}$ to 5 $hr^{-1}$ and an alkylatable aromatic:alkylating agent mole ratio of 0.5:1 to about 1:2.

15. A process for preparing long chain alkyl substituted naphthalenes comprising alkylating naphthalene with an olefin containing at least 8 carbon atoms under alkylation reaction conditions in the presence of an alkylation catalyst comprising an ultrastable Y zeolite with exchangeable sites containing both ammonium and protonic species at a molar ratio of ammonium:protonic species from 65:35 to 35:65, and wherein the zeolite is 20 to 40% Rare Earth exchanged, to form an alkylated naphthalene.

16. The process of claim 15 wherein the ratio of ammonium:protonic species is about 54 to 46 and the zeolite is 25 to 36% Rare Earth exchanged.

17. The process of claim 3 wherein the zeolite is 20% to 40% Rare Earth exchanged.

18. The process of claim 1 wherein alkylation reaction conditions include a temperature of 100° C. to 350° C., a pressure of 1 to 25 atmospheres, a WHSV of 0.5 $hr^{-1}$ to 5 $hr^{-1}$ and an alkylatable aromatic:alkylating agent mole ratio of 2:1 to about 1:2.

19. The process of claim 1 wherein the zeolite is USY.

* * * * *